(12) United States Patent
Farrelly

(10) Patent No.: US 8,460,221 B2
(45) Date of Patent: Jun. 11, 2013

(54) ULTRA-SONIC AND VIBRATORY TREATMENT DEVICES AND METHODS

(75) Inventor: Justin Nicholas Farrelly, Carrollton, TX (US)

(73) Assignee: Krypton Systems LLC, Plano, TX (US)

( * ) Notice: Subject to any disclaimer, the term of this patent is extended or adjusted under 35 U.S.C. 154(b) by 631 days.

(21) Appl. No.: 12/544,639

(22) Filed: Aug. 20, 2009

(65) Prior Publication Data

US 2011/0046521 A1    Feb. 24, 2011

(51) Int. Cl.
*A61N 7/00* (2006.01)
(52) U.S. Cl.
USPC ........................................ 601/2; 601/3; 601/4
(58) Field of Classification Search
USPC ............................................ 601/2–4; 604/22
See application file for complete search history.

(56) References Cited

U.S. PATENT DOCUMENTS

| | | | |
|---|---|---|---|
| 2,096,826 A | 10/1937 | Schrader | |
| 2,714,672 A | 8/1955 | Wright | |
| 2,824,243 A | 2/1958 | Sargeant | |
| 2,930,912 A | 3/1960 | Miller | |
| 3,060,333 A | 10/1962 | Bradley | |
| 3,075,098 A | 1/1963 | Shoor | |
| 3,146,360 A | 8/1964 | Marshall | |
| 3,233,465 A | 2/1966 | Tolliver et al. | |
| 3,283,182 A | 11/1966 | Jones et al. | |
| 3,349,259 A | 10/1967 | Kistler | |
| 3,566,163 A | 2/1971 | Fischer et al. | |
| 3,845,332 A | 10/1974 | Last | |
| 4,447,755 A | 5/1984 | Ghiurea | |
| 4,460,842 A | 7/1984 | Waanders et al. | |
| 4,471,256 A | 9/1984 | Igashira et al. | |
| 4,995,587 A | 2/1991 | Alexius | |
| 5,128,902 A | 7/1992 | Spinnler | |
| 5,159,226 A | 10/1992 | Montgomery | |
| 5,306,980 A | 4/1994 | Montgomery | |
| 5,359,252 A | 10/1994 | Swift et al. | |
| 6,308,585 B1 | 10/2001 | Nilsson et al. | |
| 6,377,693 B1 | 4/2002 | Lippa et al. | |
| 6,416,525 B1 | 7/2002 | Shibata et al. | |
| 6,578,753 B1 | 6/2003 | Sakakura et al. | |
| 6,630,768 B2 | 10/2003 | Yamashiro et al. | |
| 6,827,724 B2 | 12/2004 | Shibata et al. | |
| 6,876,128 B2 | 4/2005 | Nguyen et al. | |
| 7,145,282 B2 | 12/2006 | Oakley et al. | |
| 2001/0051776 A1* | 12/2001 | Lenhardt | 601/2 |
| 2007/0060864 A1* | 3/2007 | Redding | 604/22 |
| 2007/0063618 A1* | 3/2007 | Bromfield | 310/323.19 |
| 2007/0149881 A1* | 6/2007 | Rabin | 600/471 |
| 2008/0056960 A1* | 3/2008 | Lauharn et al. | 422/127 |
| 2009/0015104 A1 | 1/2009 | Kimura et al. | |

* cited by examiner

*Primary Examiner* — Unsu Jung
*Assistant Examiner* — Daniel Huntley
(74) *Attorney, Agent, or Firm* — John G. Fischer, Esq.; Paul D. Lein, Esq.; Scheef & Stone, L.L.P.

(57) ABSTRACT

An exemplary embodiment provides a hand-held apparatus for treatment of conditions requiring ultra-sonic or vibratory treatment. The apparatus includes a transducer, an electronic tuning circuit and a power source for powering the apparatus. The transducer has a first section axially aligned with the second section. The second section has an outer wall of pre-determined thickness surrounding an annular cavity that contains a piezoelectric stack. The electronic tuning circuit is in communication with the piezoelectric stack. The circuit is configured to tune the transducer to a target output frequency. The transducer, electronic tuning circuit and power source are at least partially contained within a common housing that is configured to be grasped by a human hand to administer treatment.

17 Claims, 5 Drawing Sheets

ULTRA-SONIC AND VIBRATORY TREATMENT DEVICES AND METHODS

BACKGROUND

1. Technical Field

The present technology relates to the field of medical treatments, and more particularly to devices and methods of treatment of the condition that require application of ultra-sonic or vibratory stimulation to nerves or other body tissue, including tinnitus, Bell's Palsy, and the like.

2. Description of the Related Art

Tinnitus is a medical condition in which the afflicted person hears a persistent ringing in one or both ears. The condition may be caused by a number of factors including but not limited to damage to the inner ear, prolonged exposure to noise, the use of certain prescription medications that have ototoxic side effects, ear infections, and nerve-related conditions. The effects of persistent tinnitus may include irritability, fatigue and depression. Tinnitus treatments vary but it has been suggested that in some cases the condition may be ameliorated by application of a noise signal that masks the tinnitus sound effect. Of course, this is not a "treatment" in the sense of ameliorating or curing the condition but merely application of another sound to "cover up" or mask the tinnitus "sound."

Sound may be regarded as a travelling wave in a medium (e.g. air) that exerts pressure on an object in its path (e.g. ear drum of a listener). Travelling waves may be set up by a variety of actions (e.g. clapping hands), mechanical equipment, natural forces (e.g. wind, rain, and thunder) and instruments (e.g. piano). Among the electro-mechanical devices that may be used to generate sound waves in a range of frequencies are transducers. These devices utilize piezoelectric elements that convert an electrical impulse to an applied pressure. Langevin transducers are well-known in the art. These transducers are often used in high frequency sonar and ultra-sonic applications. Langevin transducers most typically include three axially-aligned components: a fore section, an aft section and an axial bolt of high tensile steel that mechanically fastens and pulls the two sections together. Disk-shaped annular piezoelectric elements are located between the fore and aft sections, so that tightening the bolt, which extends though the central hole of the disks, pulls the fore and aft sections together thereby exerting compressive force on the piezoelectric elements sandwiched between the two sections causing them to activate. Other transducer designs may lack a bolt and their sections may be threaded together.

SUMMARY

An exemplary embodiment provides a hand-held apparatus for treatment of conditions requiring ultra-sonic or vibratory treatment. The apparatus includes a transducer, an electronic tuning circuit and a power source for powering the apparatus. The transducer has a first section and a second section axially aligned with the first section and directly mechanically coupled to the first section, without intervening structures. The second section has an outer wall of predetermined thickness surrounding an annular cavity that contains a piezoelectric stack. The electronic tuning circuit is in communication with the piezoelectric stack and is configured to tune the transducer to a target output frequency. The transducer, electronic tuning circuit and power source are at least partially contained within a common housing that is configured to be grasped by a human hand to administer treatment.

In another exemplary embodiment, there is provided a hand-held apparatus for self-administered treatment of a condition requiring ultra-sonic or vibratory stimulation. The apparatus has a common housing that contains a transducer, an electronic tuning circuit and a power source. The transducer has a first section having a central axis. It also has a second, substantially cylindrical, section having a surrounding outer wall defining a cavity containing a piezoelectric stack. The first and second sections are directly mechanically coupled together and may be aligned along a common axis. Moreover, the first and second sections are comprised of the same high strength metallic alloy. The electronic tuning circuit is in communication with the piezoelectric stack and is configured to tune the transducer to a frequency at which the power to the transducer peaks (i.e. the "transducer peak power"). The electronic tuning circuit includes a micro controller, drive electronics and a feedback circuit.

An exemplary micro controller applies a control signal to the drive electronics of the transducer which, in response, applies a drive signal to the transducer to operate the transducer at a target frequency. To determine the target frequency, the feedback circuit initially runs a frequency sweep in a range around a nominal frequency that corresponds to a region in which it is known that the transducer will be at peak power. This permits the circuit to select a window of frequency (e.g., about 10 to about 20 Hz) around the tuning point where the power peaks. This tuning point is then set as the target frequency and is communicated to and stored in the drive electronics. Thereafter, to maintain the frequency at the target (or "tuning") frequency, the feedback circuit interrogates and receives a first feedback signal from the transducer indicating the actual transducer frequency. Responsive to an error between an actual measured transducer frequency and the target frequency, the feedback circuit applies a corrective error signal to the micro controller. The micro controller, in response, applies a corrective control signal to the drive electronics. An electrical connector may be in communication with the micro controller to permit communication there through between the micro controller and an outside electronic device, such as a computer for programming the micro controller or debugging the device.

An exemplary micro controller may also be configured or programmed to set the number of doses in a time period and the dose time period (e.g. 60 seconds). It may also be configured or programmed to prevent over-use of the treatment device to exceed the treatment protocol, such as either the maximum dose (in seconds), and/or the number of doses per time period, such as doses per day (12-hour waking period). Further, in another exemplary embodiment, the treatment device may record the treatment protocol that the patient actually used, and this may be downloaded to another electronic device and/or transmitted to a care giver. Such recording of patient use data may improve patient compliance and provide valuable therapeutic feedback.

An exemplary embodiment provides a method of self treatment of a condition requiring ultra-sonic or other vibratory stimulation using a hand-held, portable treatment device. The method includes the step of grasping a housing of the hand-held, portable treatment device in a hand and activating the treatment device such that the device emits a target output frequency. Further, it includes the step of placing an exposed portion of a transducer of the activated tinnitus treatment device in direct contact with body tissue for a therapeutically effective period of time.

DETAILED DESCRIPTION OF THE PREFERRED EMBODIMENTS

In the specification, the term "exemplary embodiment" means an example of an embodiment of the technology.

Exemplary embodiments provide a hand-held, portable treatment device and a method of self administration of treatment of a condition requiring ultra-sonic or other vibratory stimulation of body tissue or nerves, such as tinnitus. The device has its own internal power source that may be rechargeable and is relatively small and light weight so that it can be carried in a handbag or pocket. It is therefore convenient for a person to carry with him/her and use, even outside of the home, for greater compliance with a treatment protocol or to use as required.

Effective treatment protocols may be prescribed by appropriate professional personnel, and it is expected that treatment will require application of the treatment device to stimulate the body tissue or nerve for brief periods of time, one or more times per day. For example, in the case of tinnitus, a therapeutically effective treatment may be carried out for about 60 seconds or any time period in the range from about 15 to about 90 seconds, or as prescribed, and may be applied to bony tissue behind the ear to stimulate the auditory nerve by bone conduction of the stimulating signal. The treatment may be repeated, as prescribed, a number of times per day, for example from about one to about 4 times per 12 hour waking period, to obtain beneficial results. The frequency of the applied treatment may be in the range of about 50 KHz +/−5 KHz.

Figure 1:
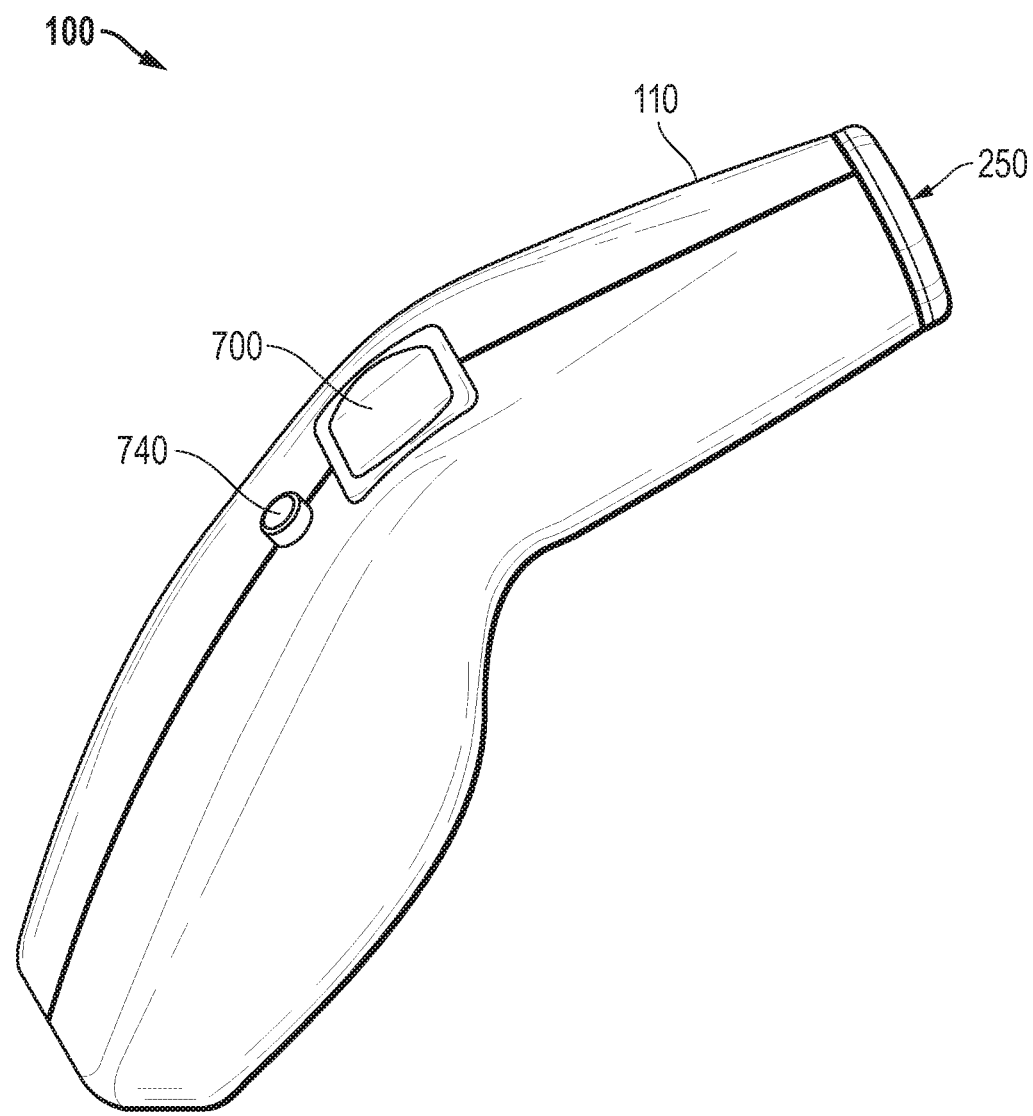
FIG. 1 is an illustrative exemplary embodiment of a hand-held, portable treatment device.

FIG. 1 shows an exemplary embodiment of a treatment device 100 that may be held in one hand, and that is self-contained, self-powered, and portable. The device 100 has a housing 110 of light-weight material, such as a polymeric material or a polymeric composite, an external switch 700, and an LED light 740 to indicate when it is activated. A front face 250 of a nose of a transducer 200 (internal, not shown) extends from one end of the device to facilitate its placement behind the ear to initiate treatment.

Figure 2:
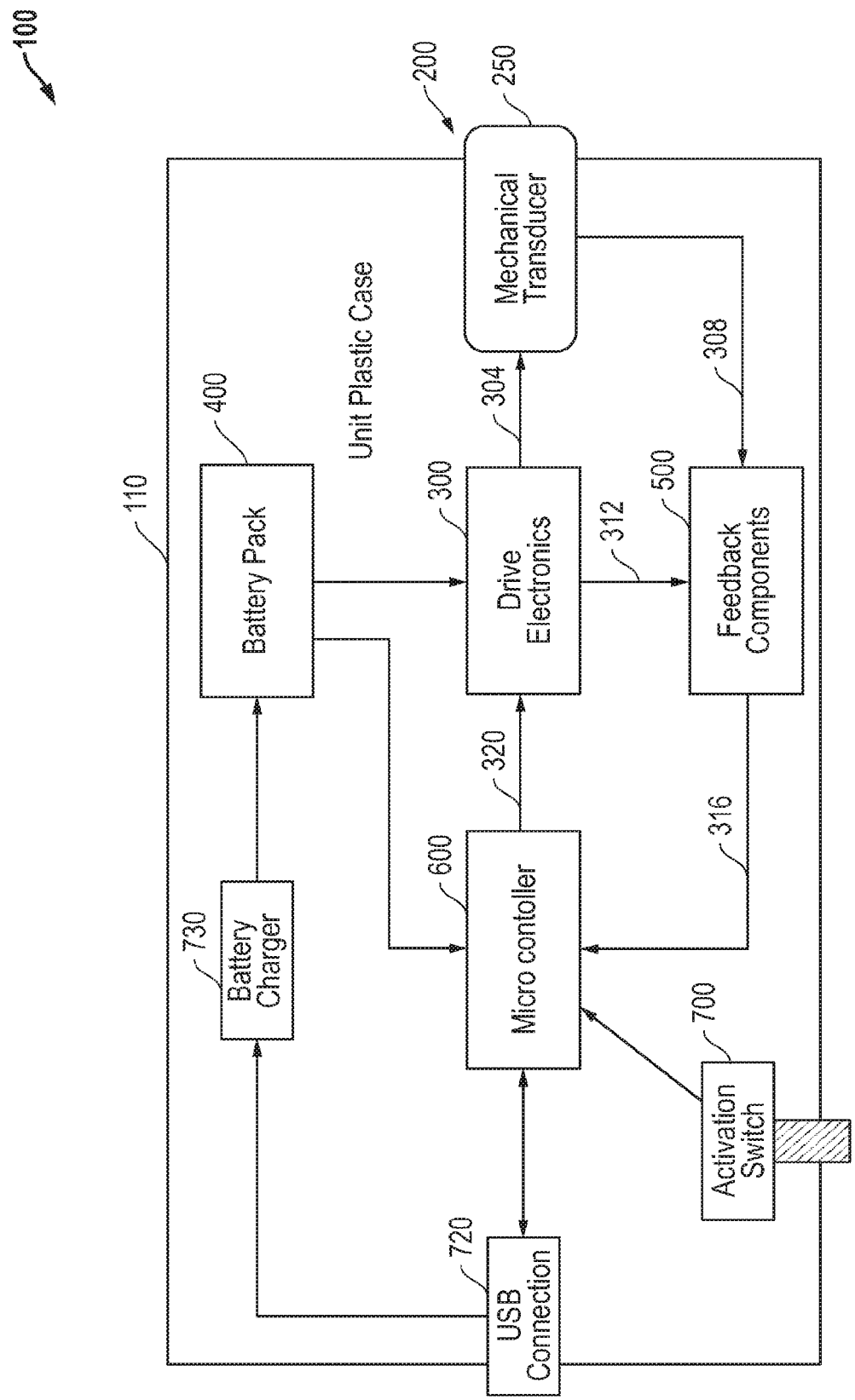
FIG. 2 is a block diagram depicting components of an exemplary treatment device.

FIG. 2 is a block diagram of an exemplary embodiment indicating electronic components that may be incorporated into a treatment device 100. Of course, some of these electronic components need not be separate as shown in this example, but may be combined into a single more complex component. The treatment device 100 includes a transducer 200 electrically connected to drive electronics 300. The transducer 200 is driven at a pre-determined or desired frequency responsive to a drive signal 304 from the drive electronics 300. The drive electronics 300 is powered by a battery pack or other power source 400.

Exemplary embodiments of a treatment device 100 include a feedback circuit 500 is configured to interrogate the transducer 200 to determine the tuning frequency of the transducer, corresponding to transducer peak power. It is also configured to transmit the determined tuning frequency as a target frequency to the drive electronics 300. The feedback circuit 500 is also configured to maintain a target frequency, once it is established. The feedback circuit 500 is accordingly configured, for example, to receive a first feedback signal 308 from the transducer 200 indicating the actual transducer frequency. The feedback circuit 500 also receives a second feedback signal 312 from the drive electronics 300 indicating the pre-determined frequency of operation. Responsive to the error between the actual frequency and the pre-determined frequency, the feedback circuit 500 applies an error signal 316 to a micro controller 600. The micro controller 600, responsive to the error signal 316, applies a control signal 320 to the drive electronics 300. Responsive to the control signal 320, the drive electronics 300 adjusts the drive signal 304 until the actual transducer frequency more closely approximates the pre-determined or desired frequency throughout the patient treatment cycle.

It will be understood by those skilled in the art that the drive electronics, the micro controller and the feedback circuit may be implemented by hardware or by a combination of hardware and software. Also, the feedback circuit 500, the drive electronics 300 and the micro controller 600 may be implemented as separate elements (e.g. discrete components) as shown in FIG. 2 or as a single, integrated component.

The micro controller 600 is activated by a switch 700 and is in communication with a connector 720, for example, a USB (universal serial bus) connector or the like. The connector 720 in the illustrated example also receives electrical input energy that is directed to battery charger 730 for recharging a rechargeable battery pack 400. Of course, the battery pack 400 may also be recharged by other means such as an (external) induction device wherein the treatment device 100 may be placed for recharging. The connector 720 may be used to connect the device 100 to an external computer (not shown in FIG. 2) for programming the micro controller 600 or debugging the device 100. Further, the treatment device may record the treatment protocol that the patient actually used, and this may also be down loaded. Such recording may improve patient compliance and provide valuable therapeutic feedback. The micro controller 600 can also be programmed to set the number of doses in a time period and the dose time period (e.g. 60 seconds), and to prevent over-use of the treatment device to exceed either the maximum set dose and/or the number of doses per time period, such as per day. The power source 400 powers the micro controller 600, the feedback circuit 500 and the drive electronics 300.

Figure 3:
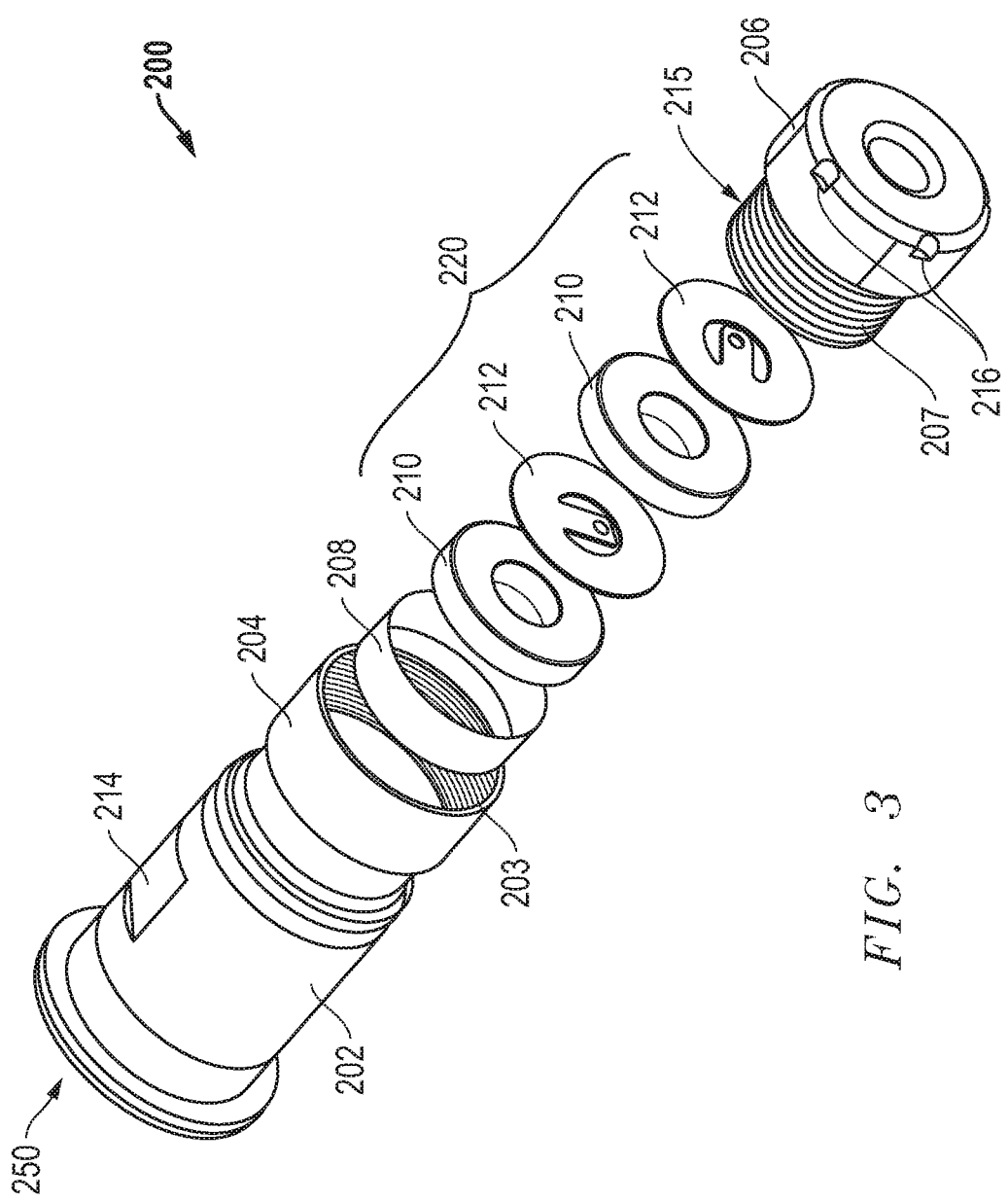
FIG. 3 is an illustration, in exploded view, of an exemplary embodiment of a transducer.
Figure 4:
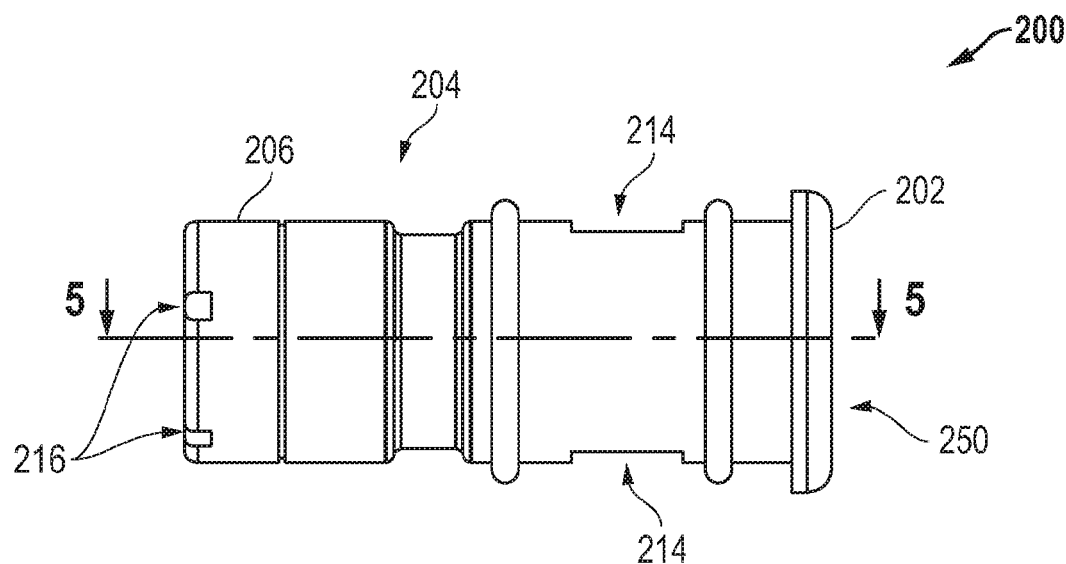
FIG. 4 is an illustration of the assembled transducer of FIG. 3.
Figure 5:
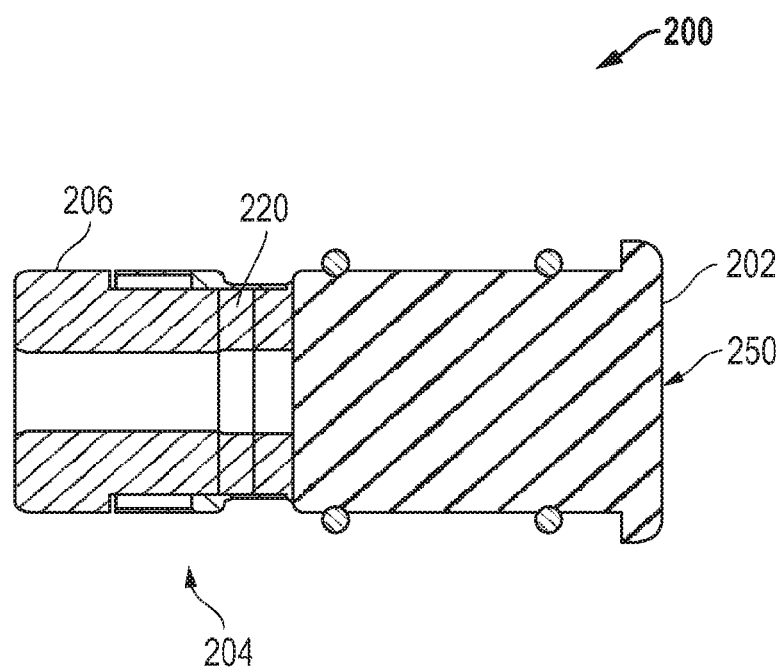
FIG. 5 is a cross sectional view through 5-5 of FIG. 4.

FIG. 3 illustrates an exemplary embodiment of a transducer 200 that may be used with embodiments of the treatment device 100. In this illustrated embodiment, the transducer has two main sections: a substantially cylindrical nose section 202 with an annular extension section 204, and a substantially cylindrical tail section 206. The two sections are threaded together by threading internal threads 203 of the nose section onto external threading 207 on the front end 215 of the tail section 206. The annular extension 204 of nose section 202 has an internal cylindrical cavity receiving a stack 220 that is surrounded by an internal dielectric or non-electrically conductive annular sleeve 208 that electrically isolates the stack 220 from the nose section 202. The stack 220 includes a series of alternating piezoelectric elements 210, such as rings or disks, and conductive elements 212, such as copper disks. Thus, when the two sections are threaded together, as shown in FIGS. 4 and 5, torque is applied with a tool. This torque application may be facilitated with the aid of optional flats 214 on the nose section 202 and optional tool-engaging machined recesses 216 on the tail section 206. As a consequence of the applied torque, the stack 220 of the series of alternating piezoelectric elements 210 and the disks 212 is compressed to a desired pressure that activates the piezoelectric stack 220.

Figure 6:
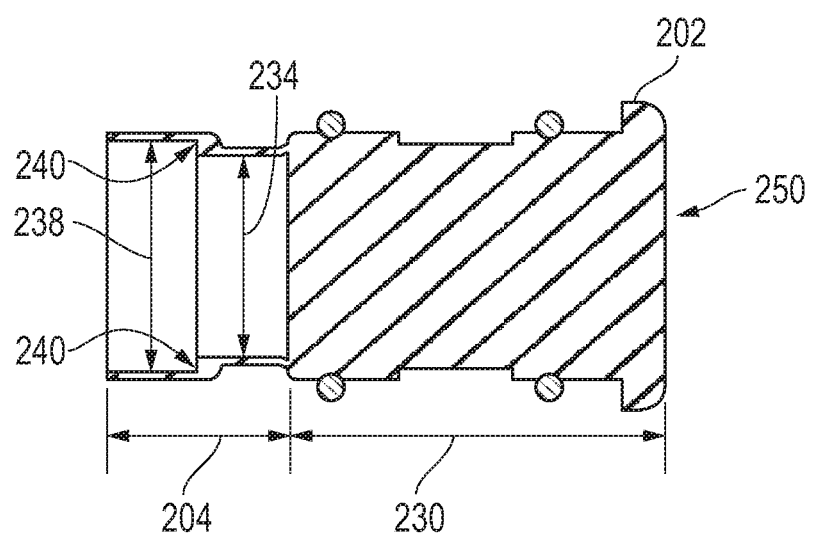
FIG. 6 illustrates a cross section through a nose section only, to show more detail, of the exemplary embodiment of FIG. 5.

The compressive force applied to the stack 220 may be better appreciated with reference to FIG. 6. As illustrated in this exemplary embodiment, the nose section 202 has a solid metal cylindrical section 230 from which extends a co-axial machined substantially cylindrical annular extension section 204. The annular extension section 204 has a first smaller internal diameter portion 234 closer to the solid metal section 230. The annular extension section 204 extends through portion 234 and has an abrupt internal diameter increase forming a second larger diameter portion 238 with a circumferential internal wall 240 separating the two portions. Thus, when the internal threads 203 of annular extension 204 is threaded to the external threads 207 of tail section 206, a front end 215 of the tail section 206 will urge up to and abut the wall 240, which effectively acts as a stop. The front end 215 of tail section 206, as seen in FIGS. 3 and 5, enters into and is threaded to the extension section 204, thereby exerting compressive force on the stack 220 inside the cavity of the annular extension section 204. Simultaneously, the applied torque forces apply tensile force to the wall of annular extension section 204.

In exemplary embodiments, the annular extension section, such as annular section 204 depicted in FIG. 3, has a wall thickness that stretches in a controlled fashion as torque (and hence tensile forces) is increased. This controlled lengthwise deformation has significance because in exemplary embodiments the overall length of the transducer has an effect on the critical frequency of the standing wave that the transducer generates. Applying torque to thread the sections of the transducer together results in applying compressive force to the piezoelectric stack and tensile force to the wall of the extension section surrounding the stack. Since the amount of compressive force applied to the stack is predetermined, and the overall length of the transducer is also predetermined (by a desired standing wave frequency), the wall thickness of the extension section, and hence its degree of lengthwise expansion under tensile stress, must be controlled to achieve both the desired compressive force on the stack and to maintain the overall transducer length, within close tolerances.

An exemplary embodiment of a transducer has all its sections fabricated from a common material, for example, high strength aeronautical grade aluminum alloys, for example AL 7075 and the like. The use of a common material ensures that sound waves (vibrations) are propagated at the same rate ("acoustic velocity") throughout the device. Moreover, the use of a common material avoids the double wave forms and distorted wave forms that are often encountered with commonplace "bolt Langevin transducers." These transducers have a steel bolt connecting and pulling together two masses, of which one may be steel and the other aluminum, with the piezoelectric stack between under compression. In contrast, exemplary embodiments of useful transducers lack a bolt and produce a wave form with a single peak frequency, which is useful in better controlling the peak frequency and applying uniform treatment to an auditory nerve of a patient.

Exemplary embodiments of the tinnitus treatment device include system electronics. An exemplary embodiment may have any one or more of the following features. Frequency generation may be carried out by a dedicated digital signal generator. Moreover, locking to a transducer peak power may be via interrogating with a digitally controlled sweep of transducer frequency, analysis of the sweep data, and modification of the generated digital signal. Power control and level setting are both controllable and may be set in the digital domain. The rechargeable battery may be monitored and charged under firm ware control. The battery may be of the NiMH-type. All aspects of the transducer performance and control may be monitored and stored in memory within the micro controller. Access to this data and reconfiguration of the treatment device may be carried out via the USB connector.

While at least one exemplary embodiment has been presented in the foregoing detailed description of the invention, it should be appreciated that a wide range of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

The invention claimed is:

1. A hand-held apparatus for treatment of conditions requiring vibratory or sonic treatment, the apparatus comprising:
   a transducer, the transducer comprising: a first section, a second section axially aligned with the first section, the second section having an outer wall of predetermined thickness surrounding an annular cavity, the first section directly mechanically connected to the second section, without any intervening structure;
   a piezoelectric stack disposed within the cavity of the second section, the piezoelectric stack comprising one or more piezoelectric disks and one or more conductive disks in alternating sequence;
   an electronic tuning circuit in communication with the piezoelectric stack, the electronic tuning circuit configured to establish a target frequency of the transducer and to maintain the target frequency; and,
   a power source powering the electronic circuit;
   wherein the first section and second section of the transducer are connected to provide a predetermined compressive force to the piezoelectric stack and create a longitudinal deformation on the outer wall of the second section; and,
   wherein the transducer, electronic tuning circuit and power source are at least partially contained within a common housing, the housing configured to be grasped by a human hand to administer treatment.

2. The apparatus of claim 1, wherein the first section and second section are comprised of high strength aluminum alloy.

3. The apparatus of claim 2, wherein a dielectric sleeve surrounds the piezoelectric stack located within the cavity.

4. The apparatus of claim 2, wherein the first section is threaded to engage threads at a first end of the second section.

5. The apparatus of claim 4, wherein the second section comprises a stop at a predetermined location to halt further axial movement of the first section during threading of the second section to the first section.

6. The apparatus of claim 1, wherein the electronic tuning circuit comprises a drive electronics operable to apply a drive signal to the transducer to drive the transducer at the target frequency.

7. The apparatus of claim 1, wherein the electronic tuning circuit comprises a feedback circuit configured to receive first and second feedback signals from the transducer and the drive electronics, respectively, the first feedback signal indicating an actual transducer frequency and the second feedback signal indicating the target frequency, the feedback circuit operable to generate an error signal responsive to the first and second feedback signals.

8. The apparatus of claim 1, wherein the electronic tuning circuit is configured to interrogate and determine a target frequency of the transducer corresponding to transducer peak power, and to maintain the transducer within a range of frequencies around the target frequency.

9. A hand-held apparatus for self-administered treatment of a condition requiring ultra-sonic or vibratory stimulation, the apparatus having a common housing comprising therein:
- a transducer comprising a first section having a central axis, a second section having a surrounding outer wall defining a cavity, the first and second sections directly mechanically coupled together, and the first and second sections comprised of the same high strength alloy;
- a piezoelectric stack disposed within the cavity of the second section, the piezoelectric stack comprising one or more piezoelectric disks and one or more conductive disks in alternating sequence;
- an electronic tuning circuit in communication with the piezoelectric stack, the circuit configured to tune the transducer to a target output frequency;
- a micro controller in communication with the electronic tuning circuit;
- a power source powering the micro controller and the electronic tuning circuit; and,
- an electrical connector in communication with the micro controller to permit communication there through between the micro controller and an outside electronic device;
- wherein the first section and second section of the transducer are coupled together to provide a predetermined compressive force to the piezoelectric stack and create a longitudinal deformation on the outer wall of the second section.

10. The apparatus of claim 9, wherein the high strength alloy is AL 7075.

11. The apparatus of claim 9, wherein the piezoelectric element is surrounded by a dielectric annular sleeve to electrically isolate the piezoelectric element from the second section.

12. The apparatus of claim 9, wherein the micro controller is pre-programmed to a therapeutic protocol comprising a predetermined dose time and number of doses, and is programmed to limit use to the therapeutic protocol.

13. The apparatus of claim 12, wherein the second section has a stop at a predetermined location to halt further axial movement of the first section during threading of the second section to the first section.

14. The apparatus of claim 9, wherein the target frequency is 51 KHz +/−5 KHz.

15. The apparatus of claim 9, wherein the electronic tuning circuit is configured to interrogate and determine a target frequency of the transducer corresponding to transducer peak power, and to maintain the transducer within a range of frequencies around the target.

16. The apparatus of claim 9, wherein the electronic tuning circuit comprises a feedback circuit configured to receive first and second feedback signals from the transducer and the drive electronics, respectively, the first feedback signal indicating an actual transducer frequency and the second feedback signal indicating the target frequency, the feedback circuit operable to generate an error signal responsive to the first and second feedback signals.

17. The apparatus of claim 16, wherein the electronic tuning circuit comprises a micro controller configured to receive the error signal and operable to apply a control signal to the drive electronics responsive to the error signal, wherein the drive electronics applies the drive signal to the transducer responsive to the error signal.

\* \* \* \* \*